US00PP13591P3

(12) United States Plant Patent
Mukherjee et al.

(10) Patent No.: US PP13,591 P3
(45) Date of Patent: Feb. 25, 2003

(54) GLADIOLUS HYBRID PLANT NAMED 'CUTE MUNNI'

(75) Inventors: Devashish Mukherjee, Himachal Pradesh (IN); Devendra Dhayani, Himachal Pradesh (IN); Jaichand Rana, Simla (IN)

(73) Assignee: Council of Scientific and Industrial Research (IN)

( * ) Notice: Subject to any disclaimer, the term of this patent is extended or adjusted under 35 U.S.C. 154(b) by 0 days.

(21) Appl. No.: 09/815,444

(22) Filed: Mar. 22, 2001

(65) Prior Publication Data

US 2002/0138889 P1 Sep. 26, 2002

(51) Int. Cl.[7] ..... A01H 5/00

(52) U.S. Cl. ..... Plt./301
(58) Field of Search ..... Plt./301

(56) References Cited

U.S. PATENT DOCUMENTS

PP227 P * 1/1937 Miller ..... Plt./301
PP2,620 P * 4/1966 Fischer ..... Plt./301

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

The invention relates to a new and distinct Gladiolus hybrid plant named 'CUTE MUNNI' characterized by its attractive Bi-color, decorative type and Mimosa Yellow flowers with Vermilion colored petal edges.

1 Drawing Sheet

BOTANICAL NAME

The present invention relates to a new Gladiolus sp. plant, in the family Iridaceae. The name of the new variety is 'CUTE MUNNI'.

BACKGROUND OF THE INVENTION

The present invention relates to a new and distinct variety of Gladiolus, a member of the Gladiolus genus. The novel plant is the hybrid between the gladiolus plants 'Bonfire', (unpatented) and 'Eurovision' (unpatented) (Hybrid Varieties) and has been named as 'CUTE MUNNI'.

Gladiolus is one of the important cut flowers throughout the world. The commercial cultivation is wide spread in temperate, tropical and subtropical climates. The demand of new varieties with better color, quality flowers, and planting materials is always existing and rising in the floriculture trade.

The applicants initiated a breeding program to develop better types of Gladiolus hybrids suitable to wide range of climatic conditions, and having wide range of characteristics such as better color, increased number of florets and spike length as per the international standards, better yield of corm and cormels, tolerant to the common diseases etc.

Accordingly the applicants initiated a breeding program involving hybridization of commonly available Gladiolus plants at the fields at Institute of Himalayan Bioresource Technology, Palampur, India in order to develop novel varieties of Gladiolus plants. In other words, the hybrids were developed by crossing parental genotypes involving sexual hybridization in the breeding program.

The program yielded a number of hybrid plants out of which one genotype namely IHBT-GH-286 was selected and named 'CUTE MUNNI'. This plant was found to have new color, flower size, number of florets per spikes, length of flower spikes, better yield of corms and cormels and less prone to common diseases. Growing the plant on a commercial scale offers the horticulturists an improved and new variety, which can be commercially cultivated.

SUMMARY OF THE INVENTION

The present invention relates to a new Gladiolus hybrid plant named 'CUTE MUNNI' belonging to the family Iridaceae. The new variety is propagated vegetatively by corms and hence can be maintained as a stable genotype. The plant of the invention is an ornamental plant widely cultivated for its beautiful flowers which are of commercial and export value.

BRIEF DESCRIPTION OF ILLUSTRATION

The accompanying photograph shows a typical specimen of the new variety, of field grown flower spike of IHBT-GH-286 ('CUTE MUNNI') designated in the illustration in color as nearly true as it is reasonably possible to make in a color illustration of this character, depicting decorative type and bi-color flowers of Mimosa Yellow (near 8B) with Vermilion, (near 41B) color petal edges. The color chart used to provide the color designations was The R.H.S. Colour chart published by The Royal Horticultural Society, London, United Kingdom.

DESCRIPTION OF THE NEW VARIETY

The new variety provides a new genotype named as 'CUTE MUNNI'. This plant has been developed through planned breeding experiments conducted at the Institute of Himalayan Resources, (IHBT) Palampur, Himachal Pradesh, India with defined aim to develop superior Gladiolus genotypes. For this purpose, Gladiolus varieties were collected from different sources and grown in the fields at Palampur, India for facilitating breeding program.

The emasculation and pollination in different varieties were carried out during the months of April and May 1991. The seeds were collected during the months of July and August 1991 and sown in beds under open field conditions and covered with dry grasses in December 1991. The resultant seedlings were space planted in the field at Palampur in March and April 1992. The cormels of survived hybrid plants were replanted continuously four years for screening and multiplication.

Based on the superior performance for attractive color combination, compactness of flower spikes, number of flowers per spikes, length of flower spikes, number of flowers remains open at a time, number of corm and cormel production per plant, the plant of this invention (IHBT-GH-286) was selected for further observation and evaluation.

Considering the superior characteristics like excellent Bi-color, number of flowers, compactness of flower spikes, plant height, ruffled-ness of flowers petals, regeneration potential and freedom from common diseases, it was asexually reproduced through corms and cormels to maintain purity.

The selected hybrid IHBT-GH-286 was named 'CUTE MUNNI' and grown at row distance of about 1 feet and plant to plant 6 inches for four consecutive years to study its growth and flowering performance and multiplication. Data was recorded on randomly selected twenty plants every year. The new variety maintained uniformity in its growth and flowering performance.

EVIDENCE OF UNIFORMITY AND STABILITY

The new variety (IHBT-GH-286) has remained stable and uniform for its morphological characters and showed consistency in performance for various growth and flowering parameters during its evaluation and vegetative multiplication since 1992. Throughout the evaluation period of the new variety, no variants were found from the normal population.

The genotype IHBT-GH-286 possesses decorative type bi-color flowers of Mimosa yellow (near 8B) with Vermilion (near 41B) color petal edges. The flowers of the plant are shown in the accompanying photographic illustration. The plant shown and described was grown under open field conditions in Palampur area of Himachal Pradesh. The altitude of Palampur is 1300 m above main sea level, which comes under sub-humid, sub-temperate zone, having an average maximum and minimum temperature of 30° C. and 10° C., respectively. The average annual rainfall is 250 cm (approximately).

The genotype IHBT-GH-286 is distinct in regeneration potential.

The plant of invention 'Cute Munni' is thus a new and distinct hybrid plant, having the following combination of characters:

A. Bi-color flowers of Mimosa yellow (near 8B) with Vermilion (near 41B) color petals edges although seed set occurs, seeds are not viable; color pattern on reverse;

B. Flowering period: about 86 days;

C. Average number of flower spikes/ plant is about 1.80;

D. Average length of flower spikes is about 104 cm.;

E. Average number of flowers per spikes is 16.6.

F. Vigor: The average growth of the plant during the growth period, i.e., from March to June (from sprouting of the bulbs to the end of flowering), is 121.24 cm. Plant height was recorded from ground level to the bottom of the last flower bud; the average is based on data collected over 5 years.

G. Plant disease resistance/susceptibility: Some incidence of Fusarium rot was noticed in the field as well as in the storage. This may be due to the high rainfall during the crop development period, because crop remains in the field during monsoon. But this variety 'Cute Munni' is performing better than many other gladiolus varieties such as 'Hunting Song' (unpatented), 'Fidelio' (unpatented), 'Her Majesty' (unpatented), 'Oscar' (unpatented), 'Red Beauty' (unpatented), etc., in this region in respect of disease incidence. This hybrid produces profuse cormels average 137/plant and corms 1.86/plant. Hence, the multiplication rate is very high.

The following is an objective description of the new variety:

Genus: Gladiolus.
Species: Hybrid.
Family: Iridacae.
Common name: Sward lily/ Gladiolus.
Average plant height: About 121 cm.
Growth habit: Erect, uniform.
Average stem diameter: About 1.17 cm.
Average number of leaves/ plant: About 7.62.
Average size of leaves: About 52.23 (height); length 39.6 to 76.2 cm (average length 54.22 cm).
Arrangement of leaves: Leaves cauline, alternately overlapped, sheathed.
Form and color of leaves: Blades sword shaped, linear, lanceolate, acute or acuminate, ventral surface darker (near 137A) than dorsal surface; smooth-glabrous, margin entire, thick, fibrous.
Bud size and color: From 4.93 cm to 7.12 cm long (bottom 3 buds were taken), with an average length of 5.79 cm; diameter of the lower 3 buds from 0.94 cm to 1.36 cm (average is 1.16 cm); color is Indian Orange (near 32 A).
Average days to flower: About 86 days.
Type of flowers: Decorative.
Average number of spikes/ plant: About 1.80.
Average length of flower spike: About 104 cm.
Average number of flowers/ spike: About 16.6.
Flower color: Mimosa yellow (near 8B) with Vermilion (near 41B) color petal edges.
Type of tepals: Slightly ruffled.
Tepals: Perianth petaloid, actinomorphic; 6 tepals, arranged in two whorls, 3 each in inner and outer whorls; imbricate estivation polyphyllous, tepals shortly stalked or sessile, base cuneate, round, apex obtuse, blunt, oblong, oblanceolate, margin entire, oblique, 4.5–5.5 cm long, 4–5 cm wide.
Androecium: Stamens triandrous arranged in a whorl, adnate to tepals, shorter than tepals and style; filaments white, slightly curved, about 3 cm long; anthers attached at the top of the filament, dithecous, purple to violet color; about 12 mm long.
Gynoecium: Ovary inferior, tricarpellary, trilocular, many ovules in each locule; style single, terminal, longer than stamens, white (pale) in color; about 5.5 to 6 cm long; stigma trilobed, lobe stalked, white color, wavy, villous.
Average number of flowers remains open at a time: About 7.91.
*Average longevity of the 1st flower.*—About 3.34 days.
*Averager diameter of 1st flower.*—About 8.90 cm.
*Average longevity of the spike.*—About 9.70 days.
*Average number of corms/plant.*—About 1.86.
*Average diameter of corms.*—About 5.61.
*Average number of cormels/ plant.*—About 137.

We claim:

1. A new and distinct Gladiolus hybrid plant named 'CUTE MUNNI' substantially as herein described and illustrated.

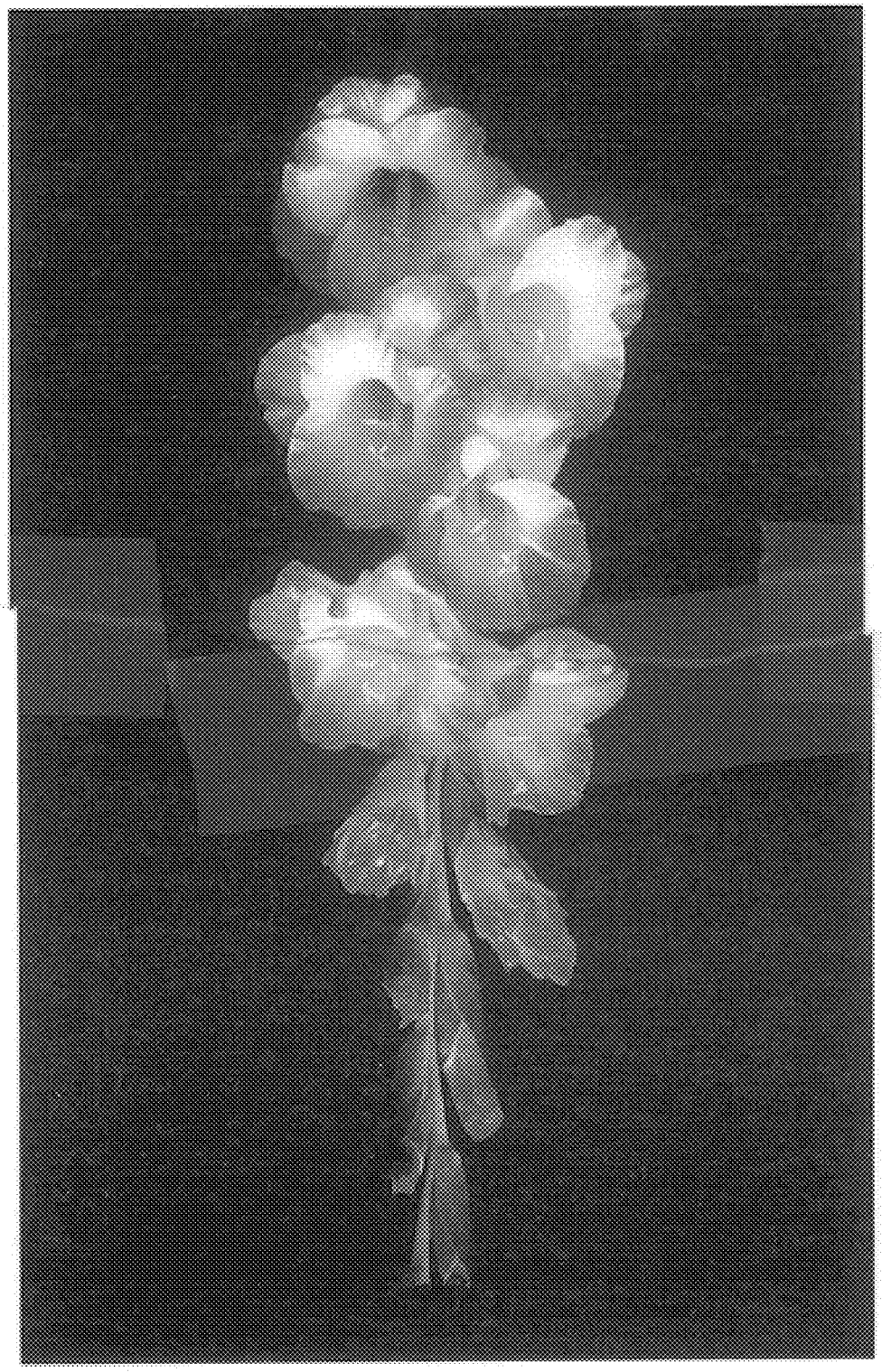

* * * * *